United States Patent
Leyendecker et al.

(10) Patent No.: US 10,111,737 B2
(45) Date of Patent: Oct. 30, 2018

(54) INTRAVAGINAL INSERT FOR INCONTINENCE MANAGEMENT

(71) Applicants: Kimberly Leyendecker, Royal Palm Beach, FL (US); Jennifer Benedict, Royal Palm Beach, FL (US)

(72) Inventors: Kimberly Leyendecker, Royal Palm Beach, FL (US); Jennifer Benedict, Royal Palm Beach, FL (US)

(*) Notice: Subject to any disclaimer, the term of this patent is extended or adjusted under 35 U.S.C. 154(b) by 60 days.

(21) Appl. No.: 15/068,457

(22) Filed: Mar. 11, 2016

(65) Prior Publication Data
US 2016/0317270 A1    Nov. 3, 2016

Related U.S. Application Data

(60) Continuation-in-part of application No. 29/534,291, filed on Jul. 28, 2015, now Pat. No. Des. 760,899, which is a division of application No. 29/467,681, filed on Sep. 21, 2013, now Pat. No. Des. 737,969.

(51) Int. Cl.
*A61F 2/00* (2006.01)

(52) U.S. Cl.
CPC .................... *A61F 2/005* (2013.01)

(58) Field of Classification Search
CPC ............... A61F 2/005; A61F 2/0009
See application file for complete search history.

(56) References Cited

U.S. PATENT DOCUMENTS

| | | |
|---|---|---|
| 4,307,716 A | 12/1981 | Davis |
| D272,945 S | 3/1984 | Suhel |
| 4,574,791 A | 3/1986 | Mitchener |
| D291,918 S | 9/1987 | Spits |
| 5,176,454 A | 1/1993 | Schlereth |
| 5,213,557 A | 5/1993 | Firth |
| 5,865,715 A | 2/1999 | Wallick |
| 6,030,338 A | 2/2000 | Benderev |
| 6,068,581 A | 5/2000 | Anderson |
| 6,110,099 A | 8/2000 | Benderev |
| D458,681 S | 6/2002 | Sherlock |
| 6,428,467 B1 | 8/2002 | Benderev |
| 6,478,726 B1 | 11/2002 | Zunker |
| 6,530,879 B1 | 3/2003 | Adamkiewicz |
| 6,770,025 B2 | 8/2004 | Zunker |
| 7,771,344 B2 | 8/2010 | Ziv |
| 7,998,056 B2 | 8/2011 | Stifter et al. |
| 8,727,961 B2 | 5/2014 | Ziv |
| 8,926,493 B2 | 1/2015 | Karapasha |
| D737,696 S | 9/2015 | Leyendecker |
| D741,479 S | 10/2015 | Agrawal |
| 2004/0084054 A1* | 5/2004 | Kaseki ............... A61F 6/08 128/885 |

(Continued)

*Primary Examiner* — Christine H Matthews
(74) *Attorney, Agent, or Firm* — Joseph W. Bain; Shutts & Bowen LLP

(57) ABSTRACT

An intravaginal insert device for the management of stress urinary incontinence is disclosed. The insert device can provide an insert body shaped for comfortable and secure placement in the vagina at a depth for support of the urethra. The insert body can be formed by a mold overlay on a plastic core that is provides with interstitial gaps to enhance the integration of the overlay with the core. The core can further provide a hitch for attachment of a tether, such as string, to facilitate removal of the insert after use.

17 Claims, 2 Drawing Sheets

(56) References Cited

U.S. PATENT DOCUMENTS

| | | | |
|---|---|---|---|
| 2007/0203429 A1* | 8/2007 | Ziv | A61F 2/005 |
| | | | 600/573 |
| 2008/0195028 A1 | 8/2008 | Hasse | |
| 2008/0228128 A1* | 9/2008 | Karapasha | A61F 13/266 |
| | | | 604/15 |
| 2009/0095304 A1 | 4/2009 | Richardson et al. | |
| 2009/0247930 A1 | 10/2009 | Fung | |

* cited by examiner

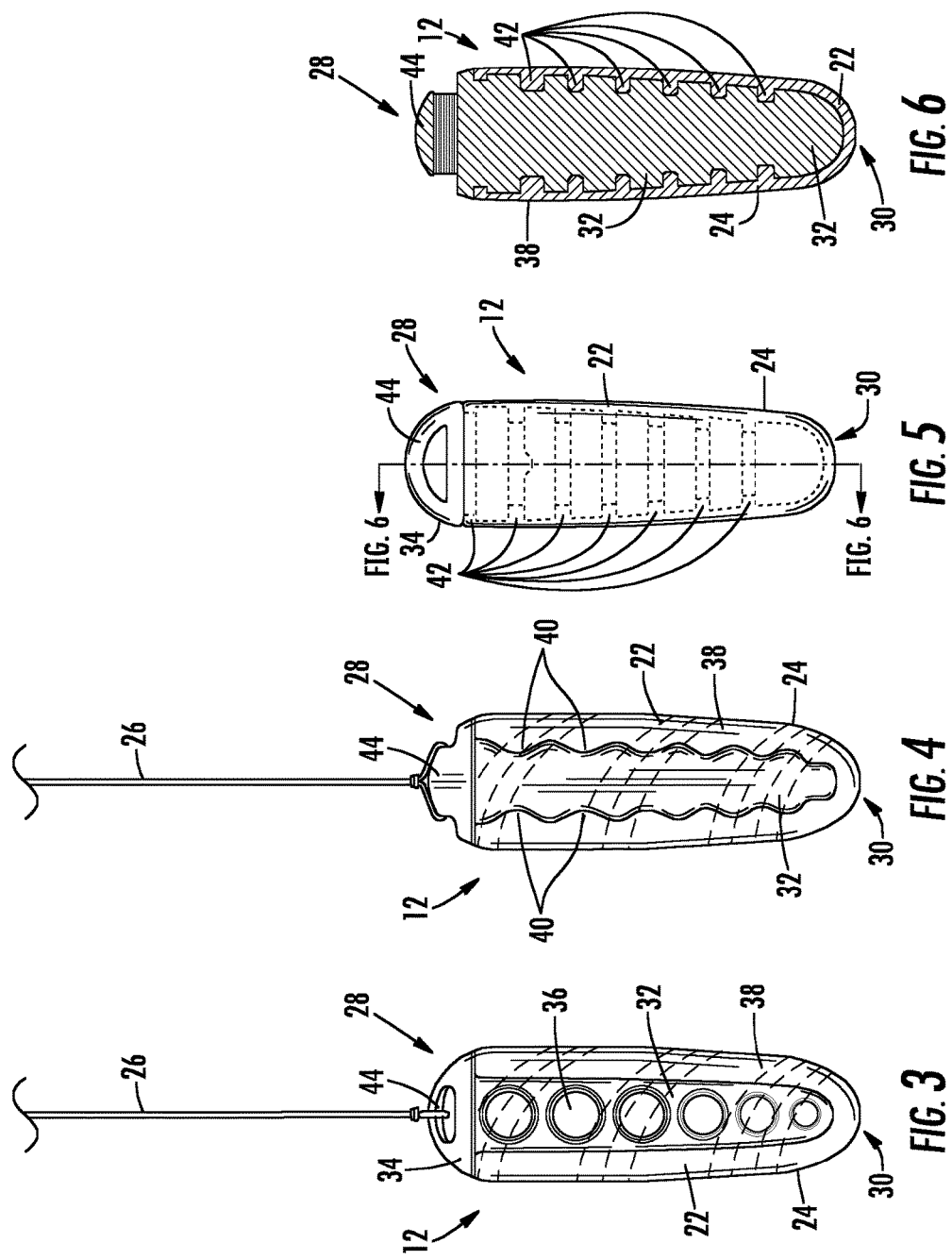

INTRAVAGINAL INSERT FOR INCONTINENCE MANAGEMENT

This application is a Continuation-in-part of U.S. application Ser. No. 29/534,291 filed Jul. 28, 2015 entitled "Female Intravaginal Incontinence Device", issued as U.S. Pat. No. D760,899 on Jul. 5, 2016 which is a division of U.S. application Ser. No. 29/467,681, filed Sep. 21, 2013 entitled "Female Intravaginal Incontinence Device", issued as U.S. Pat. No. D737,969.

FIELD OF THE INVENTION

The present invention relates to methods and devices for the management of incontinence and more particular to intravaginal inserts for incontinence management.

BACKGROUND

Stress urinary incontinence (SUI), defined as involuntary leakage of urine from the bladder accompanying physical activity which causes increased intraabdominal pressure, is a common medical problem currently affecting as many as 25 to 50 percent of women in the U.S. This condition is twice as common in women as in men. The absence of a standardized epidemiologic definition of SUI makes it difficult to establish the true prevalence of the disorder. It is known that the prevalence increases with age. Likely these estimates are underreported due to the fact that women are often too ashamed or embarrassed to discuss this issue, even with their health care providers. Urinary incontinence is associated with substantial €costs.• In addition to high economic costs, urinary incontinence results in medical and psychological morbidity and diminished quality of life. The economic costs are substantial, currently accounting for over $20 billion per year in the U.S., with a majority (50-75%) attributed to resources used for incontinence management or €routine care• such as absorbent pads, protection, and laundry. According to data collected in the SISTEr trial which included health-related quality of life assessments, women reported the impact of SUI on health-related quality of life to be similar to the impact of other chronic and debilitating medical conditions such as stroke, cancer, diabetes, back pain and dementia. Women in this trial spent a median of $500 annually out of pocket for urinary incontinence management which represented almost one percent of their annual household income, which is comparable to the mean annual out-of-pocket spending on prescription drugs for workers with health insurance benefits.

Currently, there are initial intervention options for the management of SUI. A common option is the use of absorbent pads and diapers. Behavioral training including bladder training, pelvic floor muscle exercises and electric stimulation can also be used. While these techniques can sometimes be helpful in strengthening the pelvic floor muscles in some individuals, this process can take a significant amount of dedication, time, and money.

Urethral plugs which are designed to completely occlude the urethra can be very uncomfortable, and because they are inserted directly into the urethra, carry a significant risk of infection.

Intravaginal indwelling pessaries require a prescription, an appointment with a healthcare provider for fitting, and regular doctor visits for removal/cleaning/reinsertion.

U.S. Pat. No. 7,771,344 discloses an intravaginal device for urinary incontinence that uses extending posts or arms that engage the vaginal wall to secure the device and establish a cradle to provide the intended support to the urethra.

U.S. Patent Application Publication 2009/0095304 discloses an intra-vaginal pessary device that is an approximately oval, non-absorbent device with an embedded pull string. The pessary is described as either a solid or as being hollowed out for the passage of fluids.

U.S. Pat. No. 6,770,025 discloses a molar shaped vaginal incontinence device that includes a hollowed out passage and an enlarged distal end that can collapse on itself during removal.

U.S. Pat. No. 8,926,493 discloses a non-expandable pessary device adapted to provide pressure on the user, s urethra with a pressure region of a larger diameter and a flexile region of smaller diameter and less resistant than the pressure region. This pessary has a hollow region.

Additionally, over 200 different surgical approaches have been described to treat SUI f these can result in potential complications and significant risks associated with surgery.

SUMMARY

It is an object of the invention to provide an alternative option for the management of SUI to avoid the potential embarrassment of wearing pads or diapers and eliminating the odor which can result from this common approach.

It is another object of the invention to provide a device that can help alleviate symptoms of SUI during or instead of behavioral therapy for SUI.

It is further object of the invention to address concerns with existing approaches to SUI symptom management.

An intravaginal insert can be easily and safely used to help prevent the symptoms of stress urinary incontinence in females during such activities as exercising, coughing, sneezing, laughing, or lifting. In one embodiment, the device can be manufactured with a firm, relatively more rigid or harder insert core made of, for example, acrylonitrile butadiene styrene (ABS) which is over-molded using a textured FDA-grade ethylene vinyl acetate (EVA) material, both materials being medical grade. The device can have a tapered profile that is smaller at the distal end. The narrow, distal end can be first inserted into the vagina, and the larger, proximal end can include an attached tether, such as string. The device can present an overall convex outer surface extending from one end of the insert to the other. The device is simple to insert and remove, does not require an applicator, and is comfortable to wear. The outer surface material can be textured to more securely retain the device in use.

The tether provides for ease of removal. The device provides support and stabilization of the urethra through the vagina anteriorly during any episodes of increased intraabdominal pressure to prevent urethral hypermobility, which creates increased pressure on the bladder neck area. If the pressure on the bladder exceeds the pressure in/on the urethra, urinary leakage can occur.

The outer surface shape of the device can be substantially symmetrical about a longitudinal axis and be rounded for comfort during insertion, use and removal.

A core can be substantially immovably located within the insert body. The core can be stiffer than the insert body. A harder material can be used for the core that the material for the insert body. The insert body can be a molded overlay surrounding the core. The core can have a shape that is complimentary to the outer surface shape of the insert body.

A portion of the core can be exposed at the proximal end and the tether can be attached to the exposed portion of the core.

The core can provide a series of interstitial spaces into which the insert body molded overlay extends. The interstitial spaces can be uniformly positioned along the core. The interstitial spaces can be a series of annular gaps in the core along the length of the core. Alternatively, the interstitial spaces can be holes extending laterally through the core.

Aspects of the invention provide various embodiments of an intravaginal insert that can be simply and comfortable inserted, used and removed to manage the symptoms of SUI while addressing a number of concerns with existing SUI management solutions.

BRIEF DESCRIPTION OF THE DRAWINGS

Embodiments according to aspects of the invention are described in more detail with reference to the accompanying drawings, in which:

FIG. 3 is an elevation view of the device as shown in FIG. 2;

FIG. 4 is an elevation view of an alternative embodiment according to aspects of the invention having a core with interstitial depressions;

FIG. 5 is an elevation view of an alternative embodiment according to aspects of the invention having a core with interstitial annular grooves; and FIG. 6 is a sectional view along line-6-6 in FIG. 5.

DESCRIPTION OF EMBODIMENTS

Figure 1:
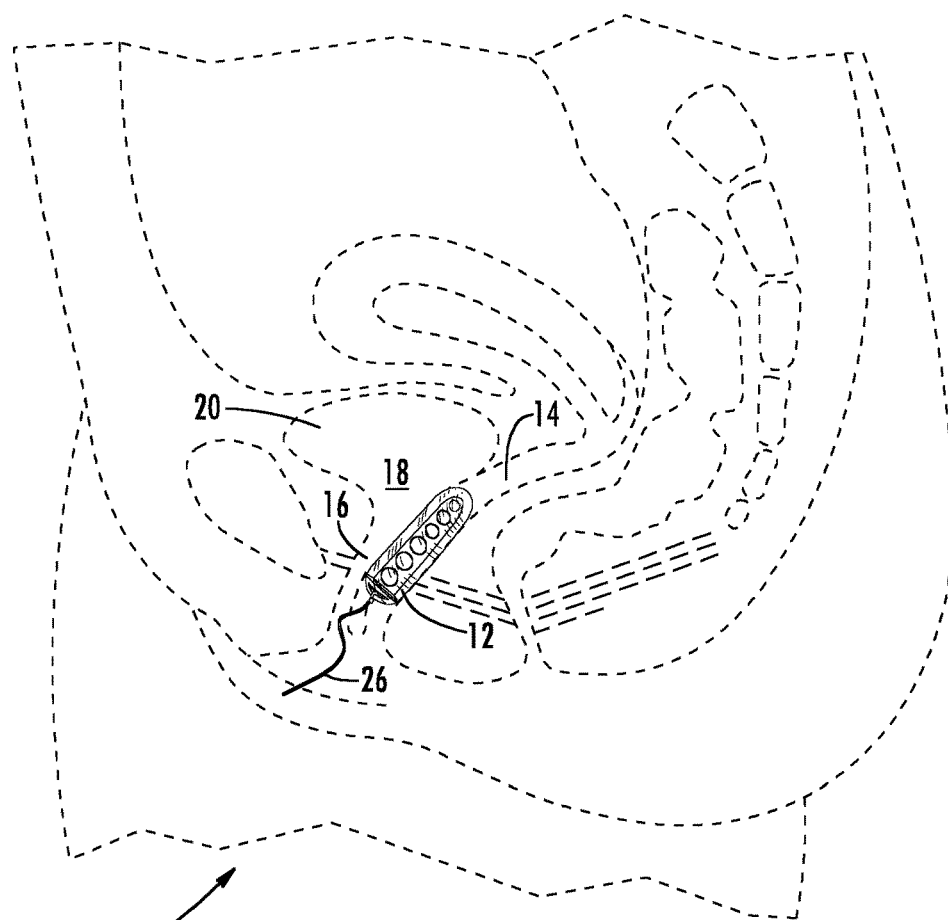
FIG. 1 is a side view showing a device according to aspects of the invention inserted intravaginally.

Referring to FIG. 1, a sectional view of a female anatomy 10 is shown. A device according to aspects of the invention in the form of an insert 12 can be positioned in the vagina 14 to support the urethra 16 anteriorly through the vagina 14 near the neck 18 of the bladder 20.

Figure 2:
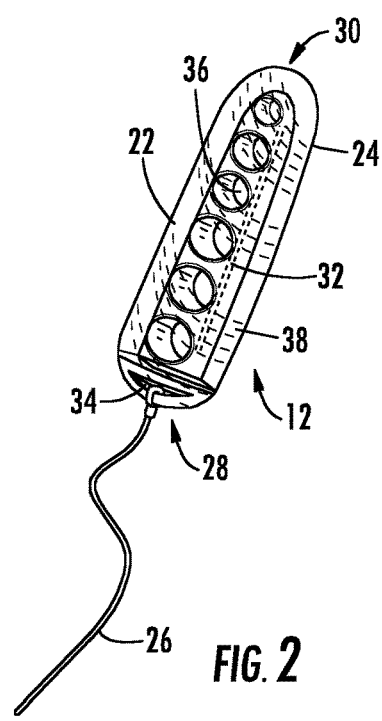
FIG. 2 is a perspective view of a device according to aspects of the invention having a core with interstitial through-holes.

According to aspects of the invention, as shown in FIG. 2, the intravaginal insert 12 for treating urinary incontinence can include an insert body 22 having an outer surface shape 24 to insert and remain secure within a vagina and a tether such as a string 26 operatively connected directly or indirectly to the insert body 22 for extending out of the vagina 14 to remove the insert body 22 from the vagina 14 after use.

The insert body 22 can have a variety of shapes so long as it is shaped to be inserted into a vagina 14 and remain secure within the vagina 14 and support the urethra 16 anteriorly through the vagina 14 when inserted.

The shape of the insert body 22 can be rounded for comfort and can have a circular cross section. Other polygonal peripheral shapes are also possible so long as the surfaces are sufficiently rounded to avoid discomfort during insertion, use and removal. The outer surface shape 24 can be symmetrical about the longitudinal axis of the insert body 22. The insert body 22 can be tapered. The insert body 22 can have a larger periphery at a proximal end 28 tapering to a smaller periphery at a distal end 30. In one embodiment, the outer surface shape 24 can be convex overall with no convex discontinuities.

The insert 12 can include a core 32 located within the insert body 22. The core 32 can be more rigid than the insert body 22 relative to an applied force in the same direction.

The core 32 can be made of a harder material than the material of the insert body 22. The core 32 provides firmness and stability to the insert body 22 to apply sufficient pressure to the urethra while permitting the insert body to be constructed with a more compliant material for comfort during insertion, use and removal. The core 32 can be substantially immovably secured in the insert body 22. That is, it is contemplated that the core 32 is substantially integrated with the insert body 22 so that there is no displacement of the core 32 relative to adjacent portions of the insert body 22, although slight elastic movements due to deformations might occur depending on the materials used.

In one embodiment, the insert body 22 can be a molded overlay surrounding the core 32. As an example, the core 32 can be made of an acrylonitrile butadiene styrene (ABS) and an FDA-grade ethylene vinyl acetate (EVA) material can be molded around the plastic core 32 in the intended shape of the insert body 22. Alternatively, the insert body 22 can be molded from silicone or material having similar properties. The insert body 22 can be constructed of a substantially non-absorbent material, meaning that the material is intended to absorb little to no liquids during periods of use, which can include, for example, a period of 8 hours or longer. The recitation of a non-absorbent material is not intended to require the complete absence of any liquid absorption but rather any liquid absorption would be considered trace. The material can be selected or modified with additives to be washable so that the insert 12 can be cleaned and reused. Alternatively, the insert 12 can be constructed of a material to be disposable.

A portion 34 of the core 32 can be left exposed at the proximal end 28 of the insert 12 and the tether 26 can be attached to the exposed portion 34 of the core 32.

The core 32 can have shape that is complimentary to the outer surface shape 24 of the insert body 22. That is, the outer surface contour of the core 32 can substantially parallel the contour of the outer surface 24 of the insert body 22. As shown in FIGS. 2 and 3, the core 32 can be solid and can provide a series of interstitial spaces, such as holes 36, into which the insert body molded overlay 38 extends during the molding process. The extension of the material of the insert body overlay 38 into the holes 36 can improve the integration of the two components 32, 38, render the core 32 substantially immovable relative to the insert body 22 and enhance the support and stabilization of the insert body overlay 38 by the core 32.

The interstitial spaces can be distributed about the core in various patterns, shapes and quantities. The interstitial spaces can be irregularly or uniformly positioned along the core. Each space can be a different shape.

As shown in FIG. 4, alternatively, the interstitial spaces can be a series of annular depressions 40 in the core 32 along the length of the core 32. The use of annular depressions 40 can reduce the possibility of sinkage or dimples in the outer surface 24 of the overlay 38 when compared to the use of through-holes 36 in the core 32. The annular depressions 40 are shown in parallel arrangement. Alternatives including a spiraling annular gap could be used.

As shown in FIGS. 5 and 6, the interstitial spaces can be a series of annular grooves 42 in the core 32 along the length of the core 32. The use of annular grooves 42 can reduce the possibility of sinkage or dimples in the outer surface 24 of the overlay 38 when compared to the use of through-holes 36 in the core 32. The annular grooves 42 are shown in parallel arrangement. Uniform spacings as shown or non-uniform spacings are possible.

The material of the core 32 is preferably harder than the material of the insert body overlay 38 and has a higher durometer than the material of the overlay 38. The material of the overlay 38 is more compliant and can be textured to provide a comfortable but more securely fitting outer surface for intravaginal placement. A durometer range of 50-80 Shore A is preferably used for the material of the overlay 38 with a higher durometer material for the core 32.

The insert 12 can be provided in different sizes and shapes. In a tapered embodiment, girth is more important than length. The girth of the insert contributes to its ability to remain secure when placed and to provide support to the urethra anteriorly through the vagina. The length of the insert 12 can enable it to be placed in position for urethral support about a finger,s length distance into the vagina. The tether such as string or cord 26 can be used to remove the insert after use. The string 26 can be secured to the insert in a variety of ways. Preferably, the string 26 is securely attached to the more rigid core 32. The core 32 can provide an attachment structure for securely connecting the string 26 to the insert 12. The attachment structure can include a hitch 44 formed at the exposed end of the core 32 to which the string 26 can be tied (as shown), crimped or otherwise secured. The string 26 can be made a medical grade material selected to be non-absorbent. A monofilament olefin or a homopolymer polyolefin material, for example, can be used for the string 26. Optionally, the tether can be formed as a braided cord.

The insert can be provided in different sizes. The insert is preferably sized to fit approximately a finger's length within the vagina. In one embodiment, the length is about 2.00-2.25 inches and tapers at an approximately 2 degree angle from a width of about 0.675 inches at the proximal end 28. The width at the distal end 30 can be reduced to around 0.600 inches. The interstitial gaps 42 can be spaced about 0.25 inches on centers and have gap widths of about 0.08 inches. The distal end 30 can be radiused about 0.219 inches and the hitch 44 can have a radius of curvature of about 0.339 inches. Alternative dimensions are also possible. The dimensions are not limited to exact numerical values as recited. Each dimension stated is intended to provide both the exact value and a functionally equivalent range surrounding the value.

The device can be provided in a €starter kit• having for example three sizes which will allow the user to determine which sized device would most comfortably fit her anatomy. Detailed instructions can be included. She can then start using the device immediately. This delivery approach can eliminate the need to seek a healthcare professional for sizing and the cost of a medical office visit. Once the size is determined, the device can be purchased in packages of each individual size. Women who are currently going untreated because of hesitance to talk about this issue and those who live with the problem because they thought surgery was their only choice to correct it will now have a safe, comfortable, convenient, and viable option.

The above descriptions of various embodiments are intended to illustrate particular aspects and elements of the invention. Persons of ordinary skill in the art will recognize that certain changes or modifications can be made to the described embodiments without departing from the scope of the invention. All such changes and modifications are intended to be within the scope of the appended claims.

What is claimed is:

1. An intravaginal insert for treating urinary incontinence, comprising:
   an insert body having an outer surface being constructed of a substantially non-absorbent material, said outer surface extending continuously between a proximal end of the insert body to a distal end of the insert body and having an outer surface shape that remains substantially unchanged to insert and remain secure within a vagina and support a urethra anteriorly through the vagina;
   a core substantially immovably secured within the insert body that is stiffer than the insert body, said insert body forming a solid volume extending from said outer surface to said core from said proximal end to said distal end; and
   a tether operatively connected to the insert body to extend out of the vagina to remove the insert body from the vagina after use.

2. The insert of claim 1, wherein the outer surface presents continuously convexly from said proximal end of the insert body to said distal end of the insert body.

3. The insert of claim 1, wherein the insert body is elongated and defines a longitudinal axis and the outer surface shape is substantially symmetrical about the longitudinal axis.

4. The insert of claim 2, wherein the outer surface shape is rounded.

5. The insert of claim 2, wherein the insert body has a larger periphery at the proximal end tapering to a smaller periphery at the distal end.

6. The insert of claim 1, wherein the insert body is a molded overlay in which the core is embedded.

7. The insert of claim 1, wherein the insert body is a molded overlay in which the core is embedded except a portion of the core is exposed at the proximal end of the insert body and the tether is attached to the exposed portion of the core.

8. The insert of claim 6, wherein the core has a shape that is complimentary to the outer surface shape of the insert body.

9. The insert of claim 6, wherein the core defines a series of interstitial spaces into which the insert body molded overlay extends.

10. The insert of claim 9, wherein the interstitial spaces are uniformly positioned along the core.

11. The insert of claim 9, wherein the interstitial spaces are holes extending laterally through the core.

12. The insert of claim 9, wherein the interstitial spaces are a series of annular gaps in the core along the length of the core.

13. The insert of claim 1, wherein the core is made of a material including acrylonitrile butadiene styrene (ABS) plastic.

14. The insert of claim 13, wherein the insert body volume is made of a material including medical grade ethylene vinyl acetate (EVA).

15. The insert of claim 13, wherein the insert body volume is made of silicone.

16. The insert of claim 1, wherein the outer surface of the insert body is textured.

17. An intravaginal insert for treating urinary incontinence, comprising:
   an insert body having an outer surface being constructed of a substantially non-absorbent material, said outer surface extending continuously between a proximal end of the insert body to a distal end of the insert body and having an outer surface shape that remains substantially unchanged to insert and remain secure within a vagina and support a urethra anteriorly through the vagina;

a core substantially immovably secured within the insert body that is made of a harder material than a material of the insert body, said insert body forming a solid volume extending from said outer surface to said core from said proximal end to said distal end; and a tether operatively connected to the insert body to extend out of the vagina to remove the insert body from the vagina after use.

* * * * *